(12) United States Patent
Majeed et al.

(10) Patent No.: US 6,436,991 B1
(45) Date of Patent: Aug. 20, 2002

(54) **COMPOSITION AND METHOD CONTAINING PRODUCTS EXTRACTED FORM *COMMIPHORA SP.* FOR PREVENTION AND TREATMENT OF ABNORMAL CELL GROWTH AND PROLIFERATION IN INFLAMMATION, NEOPLASIA AND CARDIOVASCULAR DISEASE**

(75) Inventors: Muhammed Majeed; Vladimir Badmaev, both of Piscataway, NJ (US); Rajinder Kumar Bammi, Bangalor (IN); Subbalakshmi Prakash, Piscataway, NJ (US); Sankaran Natarajan, Bangalor (IN)

(73) Assignees: Sabinsa Corporation, Piscataway, NJ (US); Sami Chemicals & Extracts (P) Ltd., Bangalor (IN)

(*) Notice: Subject to any disclaimer, the term of this patent is extended or adjusted under 35 U.S.C. 154(b) by 0 days.

(21) Appl. No.: 09/860,778

(22) Filed: May 21, 2001

Related U.S. Application Data (60) Provisional application No. 60/205,466, filed on May 19, 2000.

(51) Int. Cl.$^7$ ............................................. A01N 37/10
(52) U.S. Cl. ........................... 514/532; 560/8; 560/103; 560/104; 560/105; 560/108; 560/75
(58) Field of Search .......................... 514/532; 560/105, 560/108, 104, 103, 8, 75

(56) References Cited

PUBLICATIONS

Zhu et al, Phytochemistry, 2001, vol. 56, No. 7, pp. 723–727.*

* cited by examiner

Primary Examiner—Paul. J. Killos
Assistant Examiner—Hector M. Reyes
(74) Attorney, Agent, or Firm—Arent Fox Kintner Plotkin & Kahn, PLLC (57) ABSTRACT

Ferulate compounds derived from extracts from the plant *Commiphora wightii* are used in compositions and methods for prevention and treatment of abnormal cell growth and proliferation in inflammation, neoplasia and cardiovascular disease.

14 Claims, 5 Drawing Sheets n = 13, 15

Figure 1 n = 13, 15

Figure 2 n = 16, major fragment: m/z 299
n = 17, major fragment: m/z 313

COMPOSITION AND METHOD CONTAINING PRODUCTS EXTRACTED FORM *COMMIPHORA SP.* FOR PREVENTION AND TREATMENT OF ABNORMAL CELL GROWTH AND PROLIFERATION IN INFLAMMATION, NEOPLASIA AND CARDIOVASCULAR DISEASE

This application claims priority under 35 U.S.C. §1.119 (e) to provisional application serial No. 60/205,466, filed May 19, 2000.

FIELD OF THE INVENTION

The present invention is related to a ferulate compound and compositions thereof derived from *Commiphora wightii* or *Commiphora mukul*, Commiphora sp., and more particularly to methods of using the composition to prevent and/or treat abnormal cell growth and/or proliferation in inflammation, neoplasia and/or cardiovascular disease.

BACKGROUND OF THE INVENTION

*Commiphora mukul, Commiphora wightii,* Commiphora sp. (N.O. Burseraceae) is a branched shrub or a small tree (2–3 m high) found in some states of India and Pakistan and known to produce a resinous exudate more commonly referred to as gum guggal. The Commiphora tree is mentioned in the Classic Ayurvedic literature for use in the treatment of bone fractures, arthritis, inflammation, obesity, cardiovascular diseases and lipid disorders. The Ayurvedic medical treatises of Caraka Samhita (1000 BC), Sushruta Samhita (600 BC), Vagbhata ($7^{th}$ century AD) and Nighantusa ($12^{th}$–$14^{th}$ century AD)) disclose the effects of poor nutrition and a sedentary life style with diminished health. These two factors were reported to contribute to "coating and obstruction of channels", or to atheromatous changes including deposition of fatty streaks in the blood vessels. To counteract this pathological process, Ayurveda practitioners prescribed gum guggal obtained from the bark of the *Commiphora wightii* tree.

In the 1960's the oleogum resin (gum guggul) was studied for its potential in the treatment of elevated blood cholesterol or hyperlipidemia. This research originated from the College of Medical Sciences of Banaras Hindu Univeristy at Varanasi, India, and was continued into the 1980's at the Central Drug Research Institute (CDRI) at Lucknow, India. Based on the structure function analysis of gum guggul, it was determined that the soluble portion of the gum is ethyl acetate, and specifically its neutral portion, contained most of the hypolipidemic properties. The neutral fraction was found to be a source of sterol compounds known as gugulsterone Z and E (pregnane derivatives) and responsible for lowering of blood cholesterol. Subsequently, the preparation of gum guggul used by the CDRI in clinical studies consisted of a solid extract, standardized to contain a minimum of 2.5% guggulsterones E and Z (Indian Pharmacopea, 1988; Satyavati, 1991).

Figure 1:
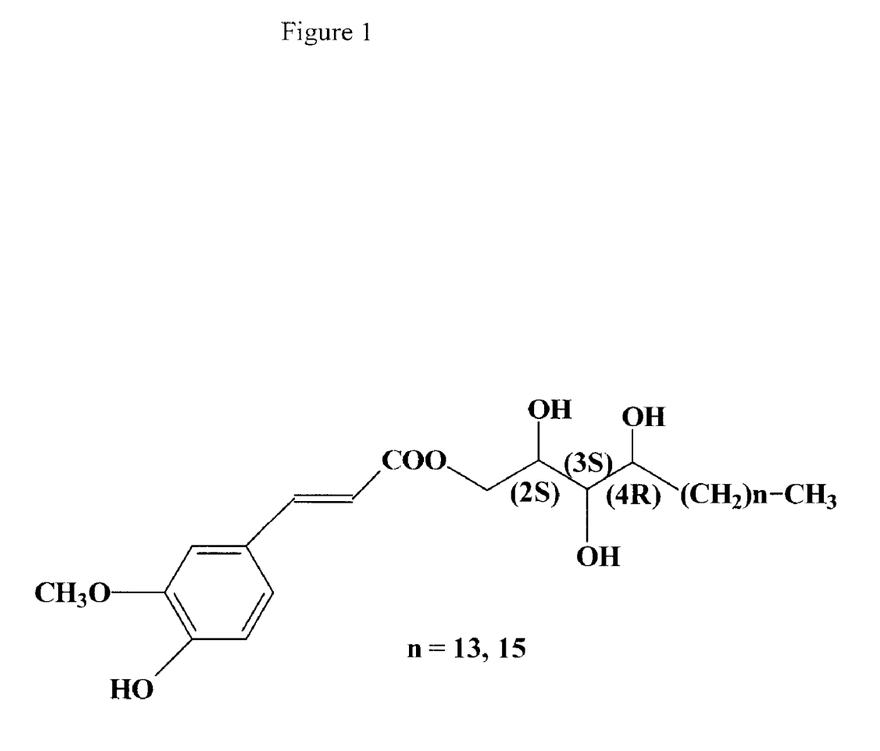
FIG. 1 shows the structures of known ferulates.

With the discovery of the hypolipidemic activity for the gum resin, several chemical investigations were undertaken. It was found that guggul resin is a complex mixture of various classes of chemical compounds such as lignans, lipids, diterpenoids and plant steroids. A waxy solid comprising a mixture of esters (FIG. 1) based on homologous long chain tetraols and ferulic acid with a unique structure, was identified in the benzene phase (Satyavati, 1991). In a more detailed study by Kumar et al. (1987), the stereochemistry of these tetraols was been determined.

The present invention relates to the purification and identification of novel ferulate compounds obtainable from gum guggul, compositions thereof, and a therapeutic use of the compositions alone or formulated to contain an ethyl acetate fraction from gum guggul comprising gugulsterones Z and E.

SUMMARY OF THE INVENTION

Based on systematic study of gum guggul, it has been found that the ethyl acetate fraction of gum guggul shows significant anti-proliferative and antioxidant effects in vitro. In embodiments of the present invention, isolation and identification of the active constituents of this plant and elucidation of their chemical structures and bioactivities is described hereunder.

An object of the present invention is the purification of a ferulate compound from an extract of gum guggul and its formulation into a composition.

Another object of the invention is a process for purifying the ferulate compound.

Another object of the invention is a method for prevention and/or treatment of abnormal cell growth and proliferation in inflammation, neoplasia and cardiovascular disease using the ferulate in a composition with or without a gum guggul extract containing gugulsterones Z and E.

DETAILED DESCRIPTION OF THE INVENTION

This invention relates to a new ferulate compound isolated from gum guggul extract. It is a new class of naturally occurring lipids which when used according to the process and method of the invention, possesses desired biological activities, i.e. anti-proliferative and antioxidant properties.

A "ferulate or ferulic acid" refers to a compound of general formula:

More preferably the ferulate compound is of formula:

wherein n is 13 or 14. Most preferably, the compound is a (z)-5-tricosene-1,2,3,4-tetraol or a (z)-5-tretracosene-1,2,3,4-tetraol of formula:

wherein n is 16 or 17.

In the present application, "biological activity" refers to cyctotoxic, anti-proliferative and antioxidant activity against a cell, more preferably a cell associated with a disease condition. Preferably, the cell exhibits abnormal cell growth.

A "disease" is a neoplasia, a neurodegenerative disease, a pulmonary disease, an inflammatory disease or a cardiovascular disease. More preferably, a neoplasia is a solid tumor, leukemia or lymphoma. More preferably, a neurodegenerative disease is Alzheimer's disease.

The ferulate compound of the present invention can be formulated into a pharmaceutical composition. The concentration for the ferulate in a unit dose can range from 0.01–300 μM, preferably, 0.1–50 μM, and more preferably, 0.3–30 μM. On a per kg basis, the concentration range is preferably 0.01 mg/kg to. 5 mg/kg, more preferably about 1 mg/kg.

A pharmaceutical composition includes pharmaceutically acceptable carriers, auxiliary substances, diluents, or fillers in addition to the ferulate compound.

The ferulate can also be reconstituted with gum guggul extract standardized to contain gugulsterones Z and E, preferably at least 2.5% by weight gugulsterones Z and E, and more preferably about 2.5% by weight gugulsterones Z and E.

The compound can be administered topically, orally or parenterally.

Cardiovascular protective effect of the ferulates.

The invention contains anti-proliferative substances that prevent the process of narrowing (stenosis) of arteries and atherosclerosis. The invention, without being limited to one specific mechanism, inhibits smooth muscle proliferation of the vessels and exerts an anti-angiogenic effect. The invention may also regulate the synthesis of the vascular endothelial growth factor (VEGF). VEGF is produced by smooth muscle cells of the vessels in response to vascular inflammation and injury, especially during hypoxia and due to action of platelet-derived growth factor, tumor necrosis factor alpha, basic fibroblast growth factor and interleukin-1 beta.

An embodiment of the invention is the stimulation of VEGF expression by the inventive ferulate compound.

VEGF exerts an anti-proliferative effect on arterial smooth muscle cells and consequently contributes to maintaining a vigorous cardiovascular system. The anti-proliferative properties of the ferulates combined with their anti-oxidant properties (i.e. prevention of LDL oxidation, Example 3 and FIG. 5) serves to enhance the previously established LDL- and trigliceryde-lowering action of gugulsterones found in gum guggul extract.

Ferulates of the present invention exert an additional anti-atherosclerotic effect on cells primarily involved in atherosclerosis, i.e., smooth muscle cells. The anti-proliferative action of ferulates on vascular smooth muscle cells attenuates the mechanism of insulin resistance and hyperinsulinemia in diabetes. Insulin resistance and hyper-insulinemia may result in stimulation of the smooth muscle cell proliferation. Insulin resistance and endothelial dysfunction are related to each other and may lead to cardiovascular diseases. Diabetes mellitus type II results in overgrowth of the smooth muscle cells and an accelerated process of atherosclerosis. In addition the inventive ferulate provides a stronger hypolipidemic effect than a composition of gum guggul extract standardized to contain at least 2.5% gugulsterones.

Role of ferulates in neurodegenerative diseases.

The concept of Alzheimer's disease as an inflammatory disease has triggered evaluation of anti-inflammatory agents in improving memory loss. A 6 month controlled trial of indomethacin in patients with the Alzheimer's disease indicated that patients in the active treatment group showed a stable level of performance, while the condition of those in the placebo group declined. Chloroquine is an intriguing possibility because it both supresses acute-phase reactants and inhibits hydrolysis of proteins within the lysosomes by raising the pH. Chloroquine may possibly prevent abnormal endosomal processing of APP leading to beta amyloid formation and neuritic plaque formation destroying memory neurons. Other agents considered include colchicine, dapsone, methotrexate, azathioprine and cyclophosphamide.

The anti-proliferative, anti-oxidant and hypolipidemic properties of the inventive ferulates provide a valid strategy in the treatment of neurodegenerative diseases, preferably, Alzheimer's disease, by preventing deposition of amyloid which destroys memory neurons, and by modulation of the abnormal phosphorylation of tau proteins (group of proteins giving raise to amyloid formation). The invention provides new composition and method of treatment of neurodegenerative diseases especially when combined with gugulsterones extracted from gum guggul.

The role of ferulates in cancer prevention and treatment.

One of the important directions of research into the mechanisms of cancer development is the link between nutrition and the cancer; in particular the association between dietary fat and the origins of human colorectal, breast, prostatic, ovarian and endometrial cancers. Many animal studies have shown a definite positive correlation between dietary fat and the rate of tumor growth and the severity of metastases. It is a recognized fact that the rate of lipid synthesis in tumor cells is quite rapid. This phenomenon can be understood, because rapidly dividing cells not only need fresh copies of DNA and proteins, but they also require the security of new biomembranes composed of phospholipids and cholesterol.

The cholesterol synthesizing pathway has been implicated as a promoter of tumor cell growth. The cholesterol intermediate, farnesyl-PP, has been implicated as a factor promoting cell proliferation. A covalently attached farnesyl group is essential for the normal functioning of the Ras protein, a key regulator of cell division in normal cells. Excessive activity of Ras produces uncontrolled cell growth, and activated Ras genes are the most frequently identified oncogenes in human tumors. Farnesyl-PP is an intermediate in the cholesterol synthesis pathway and must be synthesized de novo within the cell where it is to be used.

The other major class of lipids, fatty acids, are also involved in tumor cell growth. In fact many human and experimental cancers express elevated levels of fatty acid synthase (FAS), the major enzyme required for endogenous fatty acid biosynthesis. For example a prognostic molecule isolated from a number of breast cancer patients was identified as FAS. Inhibition of FAS leads to loss of clonogenic capacity and induction of programmed cell death in breast cancer cells.

The inventive ferulates exhibit a potent inhibitory effect on prostatic and mammary cell proliferation in vitro. It is proposed that the mechanism of this inhibition and the potential anti-cancer treatment includes:
1. blocking de novo synthesis of all cholesterol intermediates including acetyl CoA, glutamine and farnesyl-PP leading to an inability of Ras to stimulate cell growth and division; and
2. reducing the precursor supply for fatty acid synthase and thus blocking tumor cell proliferation.

The present invention is described in further detail in the following experimental details section, which sets forth specific examples to aid in understanding the invention and should not be construed to limit in any way the invention as defined in the claims which follow thereafter.

EXAMPLE 1

A Method for Isolating Compounds of the Present Invention

Methods of Chemical Analysis. TLC was performed on Sigma-Aldrich silica gel TLC plates (250 m thickness, 2–25 m particle size), with compounds visualized by $UV_{365\ nm}$ light and spraying with 10% (v/v) $H_2SO_4$ ethanol solution. Silica gel (130 B 270 mesh), Sephadex LH-20 and RP-18 (60 m) (Sigma Chemical Co., St. Louis, Mo.) were used for column chromatography. Potassium hydroxide, bis-(trimethylsilyl)-trifluoroacetamide, trimethylchlorosilane, dimethyl disulfide (DMDS), iodine and sodium bisulfite were purchased from Sigma Chemical Co. (St. Louis, Mo.). All solvents used were purchased from Fisher Scientific (Springfield, N.J.).

Equipment Used for Analysis. $^1H$ NMR and $^{13}C$ NMR spectra were obtained on a VXR-200 instrument and recorded in $CDCl_3$ with TMS as internal reference. Signals are reported in ppm δ. 2D NMR spectra were reported on a U-500 instrument (Varian Inc., Melbourne, Australia). Methanol-$d_4$ was used as solvents, and chemical shifts were expressed in parts per million δ) using TMS as internal standard. GC and GC-MS analysis were performed on a HP 6890 GC, which is equipped with a HP 5973 Mass Selective Detector. Mass spectra were run at the electronic ionization (EI) mode at standard 70 eV. The oven temperature was 100 C., raised to 200 C. at a rate of 2 C./min, held for 30 minutes, and finally raised to 280 C. at 10 C./min, the injector temperature was 270 C. and detector temperature was 280 C. The split ratio of sample was set at 60:1. DCI-MS data were obtained on a HP 59980 B particle beam LC/MS interface with HP 1090 HPLC instrument.

Plant Material. The exudates of gum guggul were obtained from Sabinsa Co. (Piscataway, N.J.) and were imported from India.

Extraction and purification. Gum guggul 2.5 kg was extracted with ethyl acetate at room temperature for one week. The plant material was filtered off and the ethyl acetate extracts were combined and concentrated under reduced pressure 850 g. A sample 100 gm was directly subjected to column chromatography on silica gel, eluted with a solvent mixture of chloroform/methanol with increasing methanol content and collected into 8 fractions (A). The Fractions of sample A5, A6 and A8 were combined to yield 13.6 gm of dry extract and then subjected to Sephadex LH-20 eluted with 95% aqueous ethanol. A total of 4 fractions (B) were collected. Among them, B3 (11 gm) showed the highest level of anti-proliferative activity and was eluted with acetone/hexane at a ratio of 2:3 on a silica gel column to give 9 fractions (C1–C9). The active fraction C8 (1.9 m) was then applied to a RP-18 column, using methanol/water (9:1) as eluent to afford an active fraction D (120 mg).

Hydrolysis of fraction D. The ferulate mixture (2–4 mg) was hydrolyzed in 1 ml of 90% methanol containing 0.4 M KOH at room temperature for 2 hrs. The resulting fatty alcohols were extracted with ethyl acetate and dried.

Trimethylsilylated (TMS) ether derivatives. The hydrolyzed sample was derivatized to form the TMS ethers with 200 μL bis-(trimethylsilyl)-trifluoroacetamide containing 1% trimethylchlorosilane. The reaction was completed in Teflon-lined screw cap tube at 75 C. for 30 minutes with a brief $N_2$ treatment prior to the reaction.

Determination of the position of the double bond. The double bond position was determined with the dimethyl disulfide (DMDS) additive method (Wang 1998). Briefly, 0.1 mL of the ethyl acetate solution of TMS ether derivatives was dried with a nitrogen stream, incubated with 0.2 mL of DMDS containing 15 mg/mL of $I_2$ at 35 C. for 30 minutes. After reduction of excess $I_2$ with saturated $NaHSO_3$ aqueous solution, 0.1 mL of ethyl acetate was added into the mixture, and after brief centrifugation, 1 μL of the upper phase was injected into the GC-MS.

Results

The MTT assay (a cell viability assay based on the tetrazolium dye method (MTT) (Scudiero et al., 1988) in MCF-7 breast tumor cells was used to isolate the bioactive fraction from gum guggul. The ethyl acetate extract of gum guggul was subjected to bioassay directed fractionation and yielded three active fractions (A5, A6 and A8) on elution with a solvent mixture of chloroform/methanol with increasing methanol content. These combined fractions were applied to a Sephadex LH-20 column which was eluted with 95% ethanol aqueous solution to yield an active fraction (B3). This fraction was then applied to a silica gel column eluted with acetone/hexane (2:3) to yield an active fraction (C8). Fraction C8 was next subjected to a RP-18 column chromatography to yield a chemically homogeneous active fraction (D).

Fraction D exhibited a red fluorescent spot under $UV_{365\ nm}$ light on silica gel $F_{254}$ plates. In the $^1H$ NMR spectrum, a group of proton signals was assigned to the feruloyl moiety [δ7.65, d, (J=15.7 Hz, H-3), δ7.06, m, (2H, H-5, 9); δ6.91, d, (J=8.0 Hz, H-8), δ6.31, d, (J=15.7 Hz, H-2) and δ3.93, s, (3H, $OCH_3$-6)] (Katagiri et al., 1997). The signals for aliphatic methylene groups δ(1.24), a terminal methyl δ(0.88, t, (J=6.9 Hz, 3H) and carbinyl methylene δ(4.37, m, 2H) were assignable to those of a long chain alcoholic residue. Three-oxygen substituted methine protons δ(3.8–4.2, 3H) indicated the presence of a highly oxygenated alcohol. Comparison of the data of D with those previously reported for guggulsterol (Kumar et al., 1987), indicated that the only big difference was the presence of two olefinic proton signals δ(5.35, m, and 5.00, m) and two allylic proton signals δ(2.01, m). Thus, D was suggested to be an unsaturated alkyl ferulate with three hydroxyl group connected to C-2', C-3', and 4'respectively. This result was supported by the $^1$H-$^1$H COSY spectrum, which displayed correlations between H-1' and H-2', and H-3' and H-4'.

Figure 2:
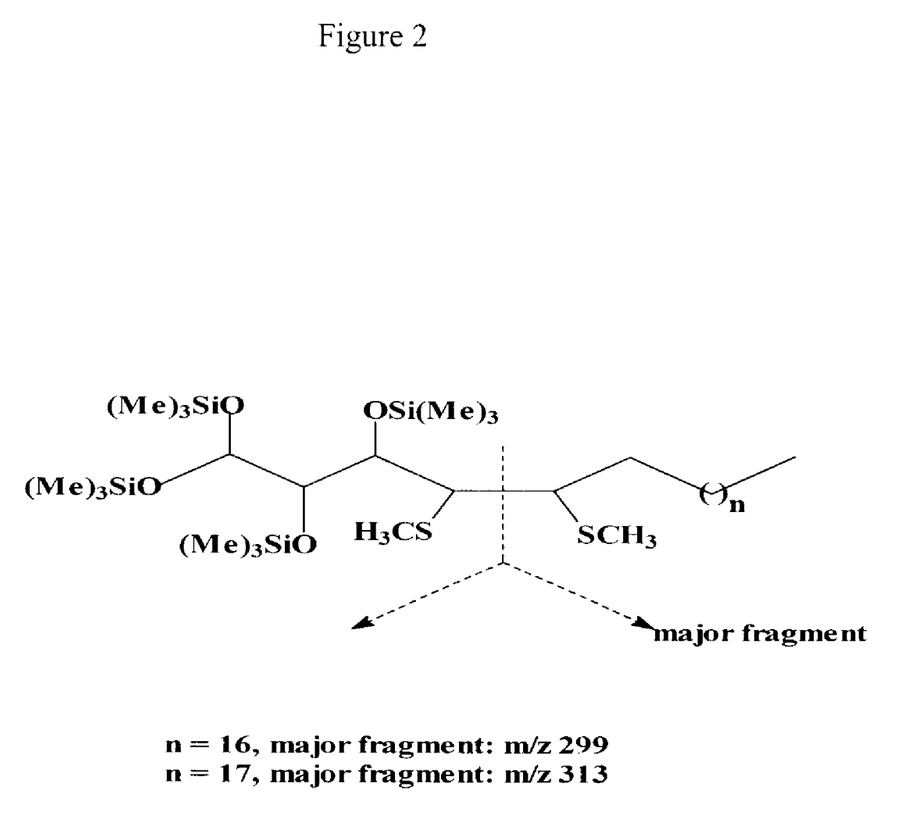
FIG. 2 shows the GC-MS fragment diagram of tetraols.

Alkaline hydrolysis of D yielded a mixture of two fatty alcohols, which were revealed by the DCI-MS data. The data showed two molecular weights 562 and 576, respectively. In order to quantify and qualify the alcohol in D, GC-MS and GC analyses were performed. Because of the substitution of multiple hydroxyl groups, the hydrolyzed alcohol mixture was first derivatized into TMS esters. Then double bond localization was carried out by GC-MS analysis of the corresponding bis(methylthio)-derivative vicinally substituted at the original double bond, which afforded an intense mass fragment arising from cleavage between the two carbons both substituted with a methylthio group (Francis et al., 1981). The resulting bis-(methylthio)-TMS esters prepared from fraction D gave two major GC peaks, D1 and D2, which indicated that the predominant alcohols in fraction D were D1 (~81%) and D2 (·19%), respectively. In the GC-MS spectra, the peak D1 $P_f$=42.0 min) showed a fragment ion at m/z 299 (100%), which suggested that the localization of bis(methylthio) substitution at C-5 and C-6. Peak D2$_{pf}$= 49.099 min) showed fragment ion at m/z 313(100%), which also suggested the localization of the bis(methylthio) substitution at C-5 and C-6(shown in FIG. 2). The double bond localization was also supported by the NMR spectra. In the $^1$H NMR spectrum, allylic proton signals indicated that only two hydrogen atoms were bonded with the double bond, while in the $^1$H-$^1$H COSY spectrum, the allylic proton signal was coupled with the signal for olefinic proton. In HMBC spectrum, the double bond localization was further confirmed by correlations of H-7' to C-5' and C-6', and of H-5' to C-7'.

The geometry of the double bonds in the alcohol was determined from analysis of the $^{13}$C NMR data. The spectrum of the mixture exhibited an allylic carbon signal at δ27.7, and was reliably assigned to the methylene carbon adjacent to a cis-double bond in aliphatic chains. The corresponding allylic methylene carbons adjacent to a trans-bond are usually observed around δ32.6. (Batchelor et al., 1974). This result suggested that the predominant alcohol in this fraction should have a cis-geometry. The absolute configuration of one of the known ferulates gugultetrol-18 was deduced as D-xylo 2S, 3S, 4R-configuration by direct comparison with synthetic compounds (Kumar and Dev, 1987). However, it was not possible to immediately determine the absolute stereochemistry of this fraction.

Figure 3:
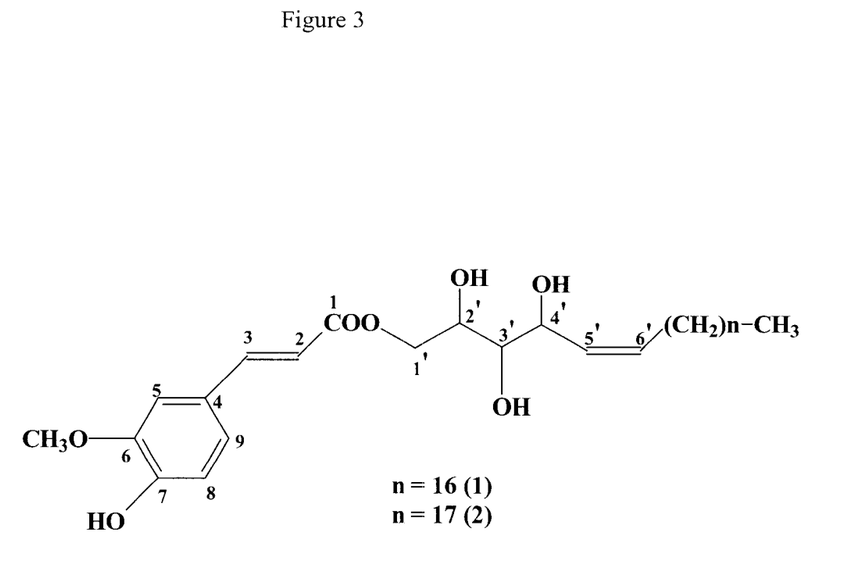
FIG. 3 shows the structures of the ferulates in accordance with embodiments of the present invention.

Combining the above information, the alcohols obtained by hydrolysis of the ferulates were concluded to be the mixture of (z)-5-tricosene-1,2,3,4-tetraol and (z)-5-tetracosene-1,2,3,4-tetraol. Structures of the major compounds in this fraction, in accordance with this invention, are shown in FIG. 3.

EXAMPLE 2

Method for Extraction of the Commiphora sp. Gum Resin Using Liquid Carbon Dioxide The ethylene acetate of Example 1 may be replaced with carbon dioxide as an extracting solvent. Preferably, carbon dioxide is one of two forms—subcritical and supercritical. The gas has a critical temp 31.2° C. and critical pressure 73.8 bars (1070 psi). The subcritical extraction is performed in the liquid state. The pressure is in the range of 300 to 700 PSI (20 to 48 bar) and temperatures ranging from 0° C. to 31° C. The supercritical extraction is performed in the fluid gas state at temperatures above critical (89° F.) 32° C. and pressure in the range of 2000 to 4000 PSI (138 to 275 bar). The supercritical process gives a higher yield in a shorter time.

For subcritical extraction, high-pressure batch or continuous extraction systems may be used. For supercritical extraction, suitable equipment includes packed or plate columns, towers featuring perforated plates or baffle structures, mixer-settler type equipment equipped with internal mixing elements, and extraction devices utilizing centrifugal force.

A batch extraction device was used, wherein the material was extracted with liquid carbon dioxide. Eighty (80) kg drums of the resin are charged into a suitable extraction chamber and contacted with carbon dioxide for 2 hours. Each 80 kg charge yielded 18 kg of a pasty material containing ferulates and other organic compounds. Subjecting the material to the process set forth in Example 1 can be used to further purify ferulates in the extracted material.

EXAMPLE 3

Analysis of the Anti-proliferative Activity

PC-3 prostate tumor cells and MCF-7 breast tumor cells were obtained from the ATCC. P388 mouse leukemia cell line and P388 cells transformed with a pHaMDR1/A retrovirus carrying an MDRi cDNA were a gift from Dr. W. Hait (Yang et al. 1994). Cells were maintained at 37° C. in an atmosphere of 5% $CO_2$ and grown in RPMI 1640 supplemented with 10% fetal bovine serum (FBS), 50 units penicillin and 50 µg/ml streptomycin. Cells were routinely checked and found to be free of contamination by mycoplasma. Cell viability was assessed by the MTT assay. Cells were plated in 96 well plates and incubated with various agents for 72 hours. Absorbance was measured at 570 nm using a Dynatech micro plate reader.

Figure 4:
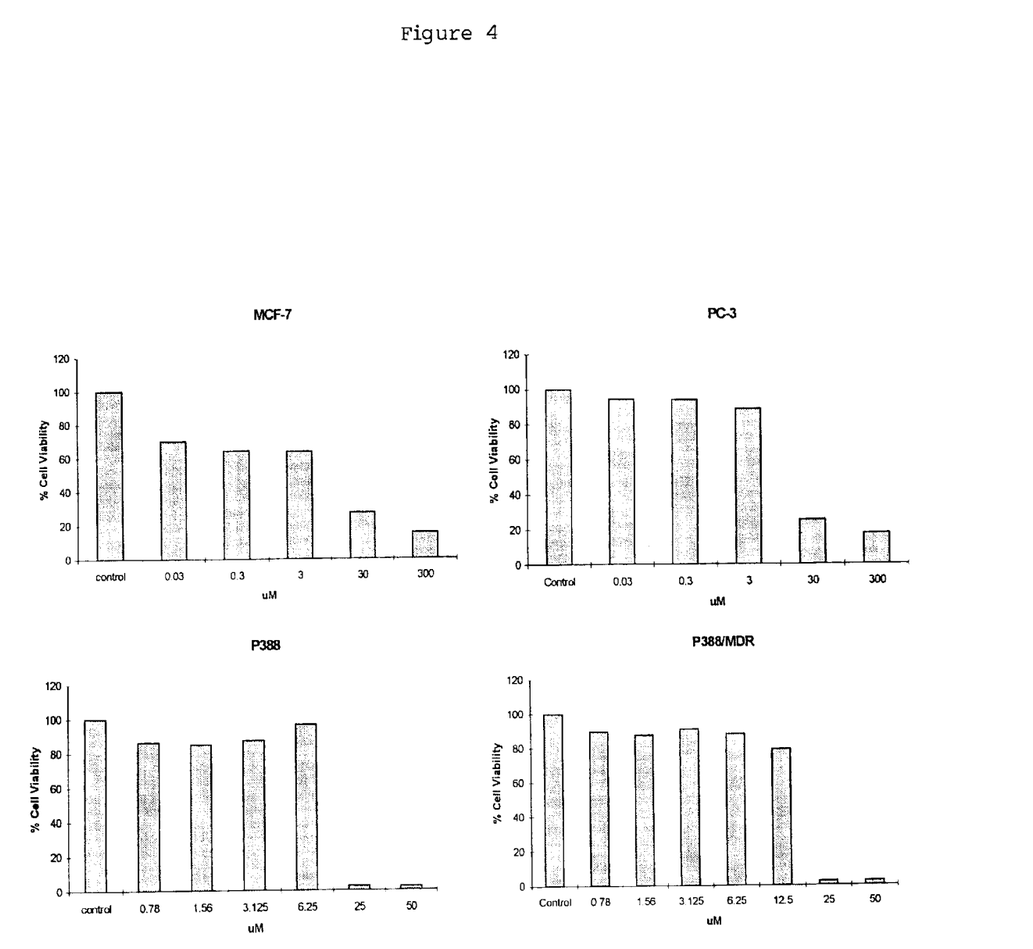
FIG. 4 shows the results from the cell viability assay by MTT measurement of MCF-7, PC-3, P388 parental and P388 cells transfected to overexpress P-glycoprotein.

As shown in FIG. 4, fraction D showed significant cytotoxic activity. Fraction D decreased cell viability in MCF-7 (breast tumor cells) and PC-3 prostate) tumor cells. The $IC_{50}$ in both cells were 14.3 mcg/ml (25 µM). To determine if fraction D could overcome a common mechanism of tumor resistance, P388 tumor cells transfected to overexpress the multidrug resistance pump P-glycoprotein were used. Fraction D decreased cell viability with $IC_{50}$<25 µM in both transfected (P388/MDR) and parental cell lines (FIG. 4). This fact suggested that this agent might be able to overcome P-glycoprotein mediated drug resistance.

EXAMPLE 4

Analysis of Antioxidant Activity

The DPPH radical scavenging assay was adapted from Chen and Ho (1995). A test fraction was added to an ethanol solution (2.5 ml) of DPPH radical (final concentration 1.0×10$^{-4}$ M). The mixtures were shaken vigorously and left to stand in the dark for 30 min. Thereafter, the absorbancy for the sample was measured using a spectrophotometer (Miltonm Roy Model 301) at 517 nm against blank samples without DPPH. The control sample was the DPPH solution without test sample. Each sample was duplicated in the test, and the values were averaged. The $IC_{50}$ was obtained by extrapolation from linear regression analysis.

Figure 5:
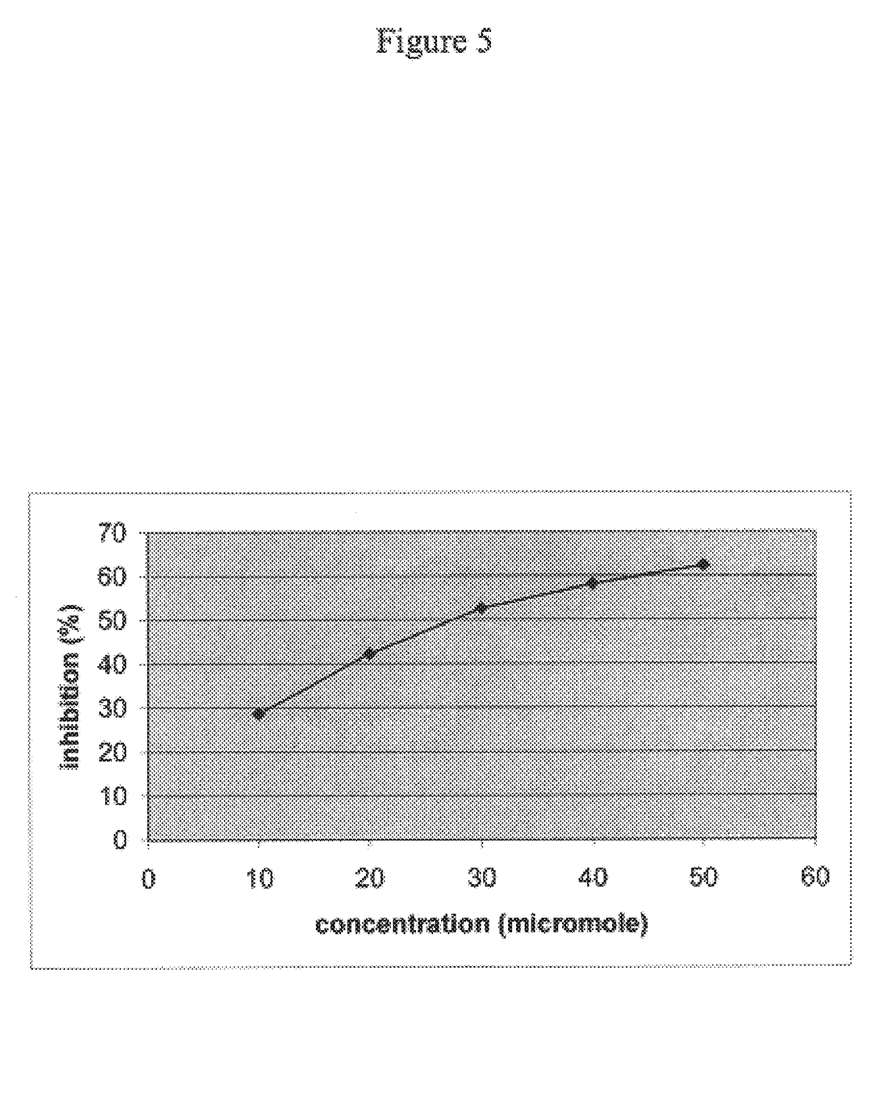
FIG. 5 shows the scavenging effect of the fraction containing the inventive ferulates on DPPH radicals.

For determining the antioxidant properties for the compound, five different concentrations of fraction D were prepared for the DPPH test (FIG. 5). The $IC_{50}$ of fraction D was determined as 16.0 mcg/ml (28 $\mu$M). Comparatively, gallic acid and catechin are essential to the antioxidant activity of tea (Chen and Ho, 1995), and their $IC_{50}$ values were reported as 10.6 $\mu$M and 18.6 $\mu$M, respectively. It was determined that the scavenging effect of fraction D on DPPH radicals was moderate compared with gallic acid and catechin.

REFERENCES

Bachelor, J. G.; Cushley, R. J.; J. H.; Carbon-13 fourier transform nuclear magnetic resonance. VIII. Role of steric and electric field effects in fatty acid spectra J. Org. Chem. 1974, 39, 1608–1075).

Chen, C. W.; Ho, C. T.; Antioxidant properties of polehenols extracted from green black teas. J. of Food Lipids. 1995, 2, 35–46.

Francis, G. W.; Veland, K.; Alkylthiolation for the determination of double-bond position in linear alkenes. J. of Chromatography. 1981, 219, 379–384.

Katagiri, Y.; Mitzutani, J.; Tahara, S.; Ferulic acid esters of unsaturated higher alcohols from Lupines luteus roots. Photochemistry. 1997, 46, 347–352.

Kumar, G. V.; Dev, S.; Chemistry of Ayurvedic curde drugs-VII. Absolute stereochemistry of gugguletrols. Tetrahedron. 1987, 43, 5933–5948.

Satyavati, G. V.; Guggulipid: a promising hypolipidaemic agent from gum guggul (*Commiphora Wightii*). Economic and Medical Plant Research. 1991, 5, 47–82.

Scudiero, D. A.; Shoemaker, R. H.; Paull, K. D.; Monks, A.; Tierney, S; Nofziger, T. H.; Currens, M. J.; Seniff, D.; Boyd, M. E. Evaluation of a soluble tetrazolium fromazan assay for cell growth and drug and sensitivity in culture using human and other tumor cell lines. Cancer Res. 1988, 48, 4827–4833.

Wang, C.; The role of lipids in disease resistance and fruit ripening tomato. Ph.D. Thesis. Rutgers University, New Brunswick, N.J., 1998.

Yang, J-M.; Goldenberg, S.; Gottesman, M. M.; Hait, W. N.; Characteristics of P388/VMDRC.04, a simple, sensitive model for studying P-Gilycoprotein antagonists. Cancer Res. 1994, 54, 730–737.

What is claimed:
1. A compound of formula:

wherein n is 16 or 17.

2. The compound of claim 1, wherein n is 16.
3. The compound of claim 1, wherein n is 17.
4. A pharmaceutical composition comprising a compound of claim 1 and a pharmaceutically acceptable carrier.
5. The pharmaceutical composition of claim 4, wherein the compound is in a range of from 0.01 $\mu$M to 300 $\mu$M.
6. The pharmaceutical composition of claim 4, further including a gum guggal extract comprising at least 2.5% gugulsterone Z and E.
7. A process for isolating the compound of claim 1, comprising the steps of extracting gum guggal with ethyl acetate; extracting a fraction exhibiting cytotoxic activity from ethyl acetate-extracted gum guggal; hydrolyzing the fraction; and thereafter extracting fatty acids from the fraction with ethyl acetate.
8. The process of claim 7, comprising extracting gum guggal with $CO_2$ in subcritical or supercritical form.
9. A method for treatment of a disease associated with abnormal cell growth, comprising administering to a subject a growth-inhibitory effective amount of a compound according to claim 1.
10. The method of claim 9, wherein the compound is administered topically, orally or parenterally.
11. The method of claim 9, wherein the disease is a neoplasia.
12. The method of claim 9, wherein the disease is an inflammatory disease.
13. The method of claim 9, wherein the disease is a cardiovascular disease.
14. The method of claim 9, wherein the disease is Alzheimer's disease.

* * * * *